(12) United States Patent
Yoshiura et al.

(10) Patent No.: US 9,227,916 B2
(45) Date of Patent: Jan. 5, 2016

(54) PROCESS FOR PRODUCING AMINO ACID

(75) Inventors: Hiromu Yoshiura, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 14/343,964

(22) PCT Filed: Sep. 12, 2012

(86) PCT No.: PCT/JP2012/073294
§ 371 (c)(1),
(2), (4) Date: Apr. 22, 2014

(87) PCT Pub. No.: WO2013/039094
PCT Pub. Date: Mar. 21, 2013

(65) Prior Publication Data
US 2014/0228593 A1    Aug. 14, 2014

(30) Foreign Application Priority Data
Sep. 12, 2011 (JP) .................................. 2011-198785

(51) Int. Cl.
*C07C 227/42* (2006.01)
(52) U.S. Cl.
CPC .................................... *C07C 227/42* (2013.01)
(58) Field of Classification Search
CPC .................................................. C07C 227/43

USPC .......................................................... 562/512
See application file for complete search history.

(56) References Cited

U.S. PATENT DOCUMENTS 5,689,001 A    11/1997    Hasegawa et al.
2009/0081739 A1    3/2009    Shimose et al.

FOREIGN PATENT DOCUMENTS

| CN | 1142488 | 2/1997 |
| CN | 101155927 | 4/2008 |
| JP | 63-575560 | 3/1988 |
| JP | 8-333312 | 12/1996 |
| WO | 2006/109830 | 10/2006 |

OTHER PUBLICATIONS

Kamei, et al., "Solid-Liquid Equilibria in an L-Isoleucine + L-Alanine + Water System", Journal of Chemical & Engineering Data, vol. 53, No. 12 (2008) 2801-06.

*Primary Examiner* — Yong Chu
(74) *Attorney, Agent, or Firm* — Fitzpatrick, Cella, Harper & Scinto

(57) ABSTRACT

L-valine granules are produced by adding L-glutamic acid to an aqueous solution containing L-valine so that the amount of L-glutamic acid is 0.5% by weight or more relative to the L-valine, dissolving the L-glutamic acid, then adjusting the pH of the aqueous solution to an acidic level and then crystallizing the L-valine.

8 Claims, 1 Drawing Sheet
(1 of 1 Drawing Sheet(s) Filed in Color)

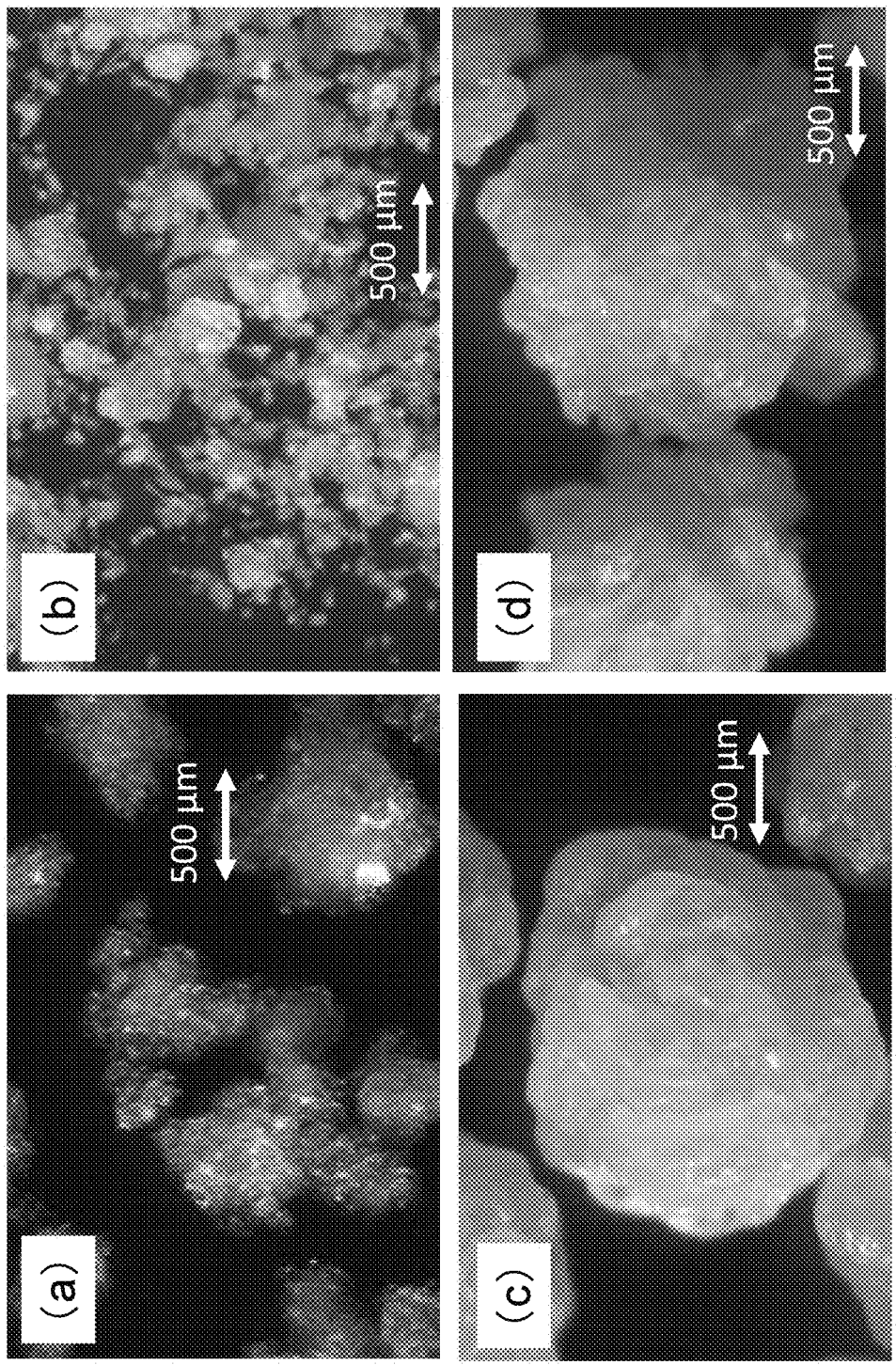

PROCESS FOR PRODUCING AMINO ACID

This application is a national phase of PCT/JP2012/073294 filed Sep. 12, 2012, which in turn claims benefit of Japanese Application No. 2011-198785 filed Sep. 12, 2011.

TECHNICAL FIELD

The present invention relates to a process for granulating L-valine.

BACKGROUND ART

When producing an amino acid by a fermentation method, the amino acid which has accumulated in the culture is recovered usually as a solid. Examples of methods for the recovery as a solid include a method which comprises removing the microbial cells from the culture, passing the residue through a resin column or the like to remove impurities thereby preparing a crude solution, conducting condensation or the like to precipitate the amino acid as crystals, and then separating the crystals from the solution (hereinafter referred to as solid-liquid separation) to recover the amino acid as crystals.

However, crystals which are, for example, flaky or in a fine powder form have a poor suitability for solid-liquid separation and necessity of a prolonged crystal drying time due to the shape thereof, and there are cases where product quality and production cost are considerably affected. In addition, such crystals which are flaky or in a fine powder form have a low specific gravity and are bulky. Thus, not only the small amount of the crystals can be packed into containers having a certain capacity and this packing is not efficient from the standpoint of transportation, but also there is a possibility that the amount of the crystals usable in final products is limited.

Examples of methods for avoiding such demerits include a method in which the amino acid to be obtained is recovered as large crystals from a solution containing the amino acid. Patent document 1 discloses a technique in which when an amino acid of interest is crystallized out after addition of seed crystals of the amino acid, the size of the amino acid crystals which are to separate out can be controlled by adjusting the particle diameter and concentration of the seed crystals. Non-patent document 1 discloses the facts that the appearance of crystals of L-isoleucine is changed by addition of L-alanine and that granules of L-isoleucine are obtained, depending on the additive amount of the L-alanine.

However, neither of the two documents discloses or suggests a feature that L-valine granules can be acquired by adding L-glutamic acid to an aqueous solution containing L-valine.

PRIOR-ART DOCUMENTS

Patent Document

Patent Document 1: International Publication WO 2006/109830, pamphlet Non-Patent Document
Non-Patent Document 1: *J. Chem. Eng. Data*, 53, 2801-2806, 2008

SUMMARY OF THE INVENTION

Problem to be Solved by the Invention

L-valine is purified as granules thereof from a culture which contains L-valine. The granulation improves suitability for solid-liquid separation and enables L-valine having a high specific gravity to be acquired.

Means for solving the Problems

The present invention relates to a process described in the following (1) to (4).
(1) A process for producing L-valine granules, comprising adding L-glutamic acid to an aqueous solution containing L-valine so that the amount of L-glutamic acid is 0.5% weight or more relative to the L-valine, dissolving the L-glutamic acid, then adjusting the pH of the aqueous solution to an acidic level and then crystallizing the L-valine.
(2) The process described in above (1), wherein the acidic level is pH 3.0 to 6.0.
(3) The process described in above (1) or (2), wherein the crystallization of the L-valine is vacuum concentration crystallization
(4) The process described in any one of above (1) to (3), wherein an L-valine concentration in the aqueous solution containing L-valine is 20 g/L or higher.

Effects of the Invention

According to the present invention, L-valine granules can be efficiently produced.

BRIEF DESCRIPTION OF THE DRAWING

The patent or application file contains at least one drawing executed in color. Copies of this patent or patent application publication with color drawing(s) will be provided by the office upon request and payment of the necessary fee.

FIG. 1 shows the shapes of L-valine granules obtained with various L-glutamic acid additive amounts. (*a*) shows the shape of L-valine granules obtained without adding L-glutamic acid, and (*b*), (*c*), and (*d*) show the shapes of L-valine granules obtained in the case of adding L-glutamic acid in amounts of 0.5% by weight, 2.0% by weight, and 4.0% by weight, respectively, relative to the L-valine.

EMBODIMENTS FOR CARRYING OUT THE INVENTION

The process of the present invention is a process for producing L-valine granules, comprising adding L-glutamic acid to an aqueous solution containing L-valine so that the amount of L-glutamic acid is 0.5% weight or more relative to the L-valine, dissolving the L-glutamic acid, then adjusting the pH of the aqueous solution to an acidic level and then crystallizing the L-valine.

Examples of the L-valine granules in the present invention include L-valine granules having such a size that when a plurality of granules thereof are examined for particle diameter with a microscope, the average particle diameter thereof is 100 μm or larger, preferably from 200 μm to 3 mm, more preferably from 250 μm to 2 mm, even more preferably from 500 μm to 1 mm.

The aqueous solution containing L-valine can be prepared by a fermentation method in which a microorganism having the ability to produce L-valine is cultured in a culture medium to produce and accumulate L-valine in a culture. However, methods for preparing the aqueous solution are not limited to the fermentation method, and the aqueous solution may be prepared, for example, by a synthesis method. The L-valine-containing aqueous solution prepared by the fermentation method may be an aqueous solution obtained by removing insoluble matter, such as the microbial cells, contained in the culture by centrifugal separation, membrane treatment, or the like, and may be an L-valine-containing aqueous solution which has been further purified using an ion-exchange resin or the like.

The L-valine concentration in the aqueous solution containing L-valine may be any concentration so long as the L-valine is granulated by adding glutamic acid thereto and conducting a crystallization operation. Examples of the aqueous solution include solutions having an L-valine concentration of preferably 20 g/L or higher, more preferably 30 g/L or higher, even more preferably 40 g/L or higher, especially preferably 50 g/L or higher.

L-Glutamic acid is added to the L-valine-containing aqueous solution so that the amount thereof relative to the L-valine is 0.5% by weight or more, preferably 1.0 to 6.0% by weight, more preferably 1.5 to 5.0% by weight, even more preferably 2.0 to 4.0% by weight. The higher the concentration of L-glutamic acid in the solution is, the larger the size of the L-valine granules to be obtained by the subsequent crystallization operation is, and the more the amount of L-glutamic acid to be simultaneously crystallized out by the crystallization operation is as well. Consequently, when the amount of L-glutamic acid which comes into the L-valine granules is desired to be reduced, the amount of the L-glutamic acid to be added can be controlled in accordance with an allowable inclusion amount of L-glutamic acid.

The L-glutamic acid to be added may be solid, or may be an aqueous solution of L-glutamic acid. When L-glutamic acid has been added, the solution may be heated according to need in order to dissolve either the L-valine or the L-glutamic acid contained in the solution.

When L-glutamic acid is added to the aqueous solution of L-valine, it is preferred to add the L-glutamic acid while stirring the solution.

It is preferred that after the addition of L-glutamic acid, the pH of the aqueous solution should be adjusted to an acidic level. Specifically, the pH thereof is adjusted to 3.0 to 6.0, preferably 3.5 to 5.0, more preferably about 4.0. For the pH adjustment, sulfuric acid can, for example, be used.

After the pH adjustment, a crystallization operation is conducted to form granules of the L-valine. The crystallization may be conducted by any method whereby L-valine granules are obtained, for example, a method in which an organic solution, such as ethanol or butanol, is added or a method in which the aqueous solution is cooled. However, crystallization by vacuum concentration is preferred.

In the case where vacuum concentration was conducted, the concentrated solution obtained is held at a constant temperature, such as 10 to 30° C., preferably 15 to 25° C., more preferably about 25° C., for 30 minutes to 15 hours, preferably 1 to 10 hours, more preferably 2 to 8 hours. Thus, the granules can be ripened.

By subjecting the concentrated solution containing granules to solid-liquid separation by an operation, such as centrifugal separation, granules of L-valine can be obtained.

The granules obtained by the separation may be washed with an aqueous solution, thereby removing impurities adherent to the surface thereof.

EXAMPLE 1

Acquisition of L-Valine Granules by Addition of L-Glutamic Acid

L-Glutamic acid, L-alanine, or L-arginine acid (each being an amino acid having a purity of 99.0% manufactured by Kyowa Hakko Bio Co., Ltd.) was added into a 1,000-mL glass vessel which contained 100 mL of 50 g/L aqueous L-valine solution (obtained by dissolving L-valine having a purity of 99.0% manufactured by Kyowa Hakko Bio Co., Ltd., in 100 mL of distilled water), in a concentration of 2.0% by weight relative to the L-valine. The contents were stirred, while being kept at 60° C., until the L-valine and the added amino acid were completely dissolved. Then, the aqueous solution was gradually cooled to 30° C.

Sulfuric acid or 5 mol/L sodium hydroxide was added to the aqueous solutions to adjust the pH of each solution to 4.0.

Subsequently, each glass vessel was sealed, the temperature was elevated to 80° C., and the pressure was reduced, thereby conducting vacuum concentration. The aqueous solution which had undergone the vacuum concentration was rapidly cooled to 25° C. and allowed to stand at this temperature for 5 hours.

As a result, granules of L-valine were formed in the solution to which L-glutamic acid had been added. However, in the solutions to which the other amino acids had been added, L-valine was able to be obtained only as microcrystals.

EXAMPLE 2

Concentration of L-Glutamic Acid and Formation of L-Valine Granules

The same procedure as in Example 1 was conducted, except that no amino acid was added or L-glutamic acid was added to the aqueous L-valine solution in a concentration of 0.5, 2.0, or 4.0% by weight, in place of adding L-glutamic acid, L-alanine, or L-arginine acid.

Whether granules had been formed or not was ascertained with a microscope (Keyence Digital microscope VHX-900). As a result, it was ascertained that L-valine is granulated in the case where L-glutamic acid was added in a concentration of 0.5% by weight or higher, as shown in FIG. 1.

EXAMPLE 3 pH of the Solution and Formation of L-Valine Granules

The same procedure as in Example 1 was conducted, except that L-glutamic acid was added as the only amino acid in place of adding L-glutamic acid, L-alanine, or L-arginine acid and that the pH of the aqueous solution was thereafter adjusted to 4.0, 7.0, or 10.0.

As a result, granules were formed at pH 4.0. However, at pH 7.0 and pH 10.0, no granules were formed and only microcrystals of L-valine were yielded.

INDUSTRIAL APPLICABILITY

According to the process of the invention, it has become possible to industrially produce granules of L-vainer, which are easy to handle.

The invention claimed is:
1. A process for producing L-valine crystal granules, comprising:
   adding L-glutamic acid to an aqueous solution containing L-valine so that the amount of L-glutamic acid is 0.5% by weight or more relative to the L-valine;
   dissolving the L-glutamic acid;
   then adjusting the pH of the aqueous solution to an acidic level; and
   then precipitating the L-valine as crystals.
2. The process according to claim 1, wherein the acidic level of the aqueous solution is pH 3.0 to 6.0.

3. The process according to claim 1, wherein the precipitation of the L-valine is conducted under reduced pressure.

4. The process according to claim 1, wherein L-valine is present in the aqueous solution at 20 g/L or higher.

5. The process according to claim 2, wherein the precipitation of the L-valine is conducted under reduced pressure.

6. The process according to claim 2, wherein L-valine is present in the aqueous solution at 20 g/L or higher.

7. The process according to claim 3, wherein L-valine is present in the aqueous solution at 20 g/L or higher.

8. The process according to claim 5, wherein L-valine is present in the aqueous solution at 20 g/L or higher.

\* \* \* \* \*